United States Patent [19]
Muehllehner et al.

[11] 3,955,088
[45] May 4, 1976

[54] POSITRON IMAGING DEVICE WITH PLURAL COINCIDENCE CHANNELS AND GRADED RADIATION ABSORPTION

[75] Inventors: Gerd Muehllehner, Mount Prospect; Ronald J. Jaszczak, Arlington Heights, both of Ill.

[73] Assignee: G. D. Searle & Co., Skokie, Ill.

[22] Filed: Oct. 2, 1974

[21] Appl. No.: 511,285

[52] U.S. Cl. ............... 250/363 S; 250/367; 250/369
[51] Int. Cl.² .......................... G01T 1/20
[58] Field of Search ......... 250/361, 362, 363, 366, 250/369, 505, 510, 515

[56] References Cited
UNITED STATES PATENTS

| | | | |
|---|---|---|---|
| 3,573,458 | 4/1971 | Anger | 250/369 X |
| 3,752,981 | 8/1973 | Jaszczak | 250/369 X |

*Primary Examiner*—Davis L. Willis
*Attorney, Agent, or Firm*—Walter C. Ramm; Peter J. Sgarbossa; Helmuth Wegner

[57] ABSTRACT

A scintillation camera system for use in positron imaging in which radiation scattered in an object under study is screened and Compton events, as well as primary radiation, are imaged.

7 Claims, 3 Drawing Figures

POSITRON IMAGING DEVICE WITH PLURAL COINCIDENCE CHANNELS AND GRADED RADIATION ABSORPTION

The present invention relates to an imaging device for detecting radiation emanating from positron annihilations, and for imaging the detected radiation to determine the distribution of radiation in an object under study.

BACKGROUND OF THE INVENTION

Scintillation camera systems for use in positron imaging have been employed for purposes of medical diagnosis to only a limited extent in the field of nuclear medicine. An early description of a positron imaging device employing scintillation crystals was disclosed in a report by Hal O. Anger printed for the U.S. Atomic Energy Commission entitled "Scintillation and Positron Cameras" (UCRL-8640, Aug. 12, 1959). The underlying concept of a scintillation camera is set forth in U.S. Pat. No. 3,011,057. The positron imaging scintillation camera system described in the aforesaid report is a particular application of a scintillation camera system in which alterations and modifications to a basic scintillation camera system are employed to enable detection of positron events. Investigation was undertaken into possible techniques and instrumentation which might be advantageously employed in scintillation camera systems for positron imaging. The results of some of these investigations are reported in: Anger, H. O.: *Radioisotope Cameras: Instrumentation in Nuclear Medicine*, Vol. 1, Hine, G. J. editor, New York, Academic Press, 1967; Brownell, G. L., Burham, C. A.: Recent Developments in Positron Scintigraphy: Instrumentation in Nuclear Medicine, Vol. 2, Hine, G. J. Sorenson, J. A., editors, New York, Academic Press, 1973; and Kenny, P. J.: *Spatial Resolution and Count Rate Capacity of a Positron Camera: Some Experimental and Theoretical Considerations: International Journal of Applied Radiation and Isotopes*, Vol. 22, Permagon Press, pp. 21-28, 1971. The results of these investigations have produced the conclusions that the useful count rate of a positron camera is only a small fraction of the actual count rate. This conclusion has been based largely on the proposition that only the photopeak produced by the two 511 KeV gamma rays emitted after the decay of a positron may be used to register a radioactive distribution of positron events within a subject of interest. In a conventional positron imaging system, two scintillation detectors are positioned on opposite sides of a subject of interest. Typically, the subject under investigation is an organ of interest of a living human being lying in a prone position. One of the scintillation detectors is positioned above the subject while the other is positioned beneath. Each of the scintillation detectors is comprised of a disc of sodium iodide, typically one-half an inch in thickness, viewed by an array of photomultiplier tubes which detect scintillations occurring in the crystal and generate electrical pulses in response thereto. The electrical pulses from both detectors are used to calculate the location of the activity for a particular plane through the subject of interest. In contradistinction to low energy gamma rays, where approximately 90% of all gamma rays contribute a count to the photopeak, only about 17% of the positron gamma rays are in the 511 KeV photopeak. About 18% of the positron gamma rays undergo Compton scatter in the crystal followed by escape of the secondary photon, and the rest penetrate a one-half inch thick sodium iodide scintillation crystal without any kind of interaction. The degree to which positron annihilations yield useful information is further reduced by the requirement in a positron imaging system for coincident detection of the two gamma rays emitted by the positron. When a positron is annihilated in the subject, two gamma rays of 511 KeV energy are produced which travel in approximately opposite directions. Since only a relatively small fraction of the positron annihilations are detected, it is particularly important to distinguish the detected positron events from background radiation. This is done through the requirement for coincidence. In addition, the requirement for coincidence is also necessary when it is desired to locate and distinguish between planes at which positron events occur. A system for accomplishing this latter object is disclosed in U.S. Pat. No. 3,573,458.

SUMMARY OF THE INVENTION

Because of the relatively low yield of useful information which has heretofore been achieved using positron imaging systems, positron imaging has heretofore been useful only for extremely low count rates of useful radiation. The high activity of the radiation source required (due to the large portion of unused radiation) has taxed the capability of pulse processing in scintillation camera systems. Accordingly, it is an object of the present invention to derive more useful information from a positron radiation source than is achieved using other conventional devices.

Furthermore, it is an object of the present invention to limit the radiation dosage which must be injested by a patient in order to obtain useful information in positron imaging.

It is a further object to distinguish between radiation resulting in Compton interaction in a scintillation crystal, and radiation scattered within an object under study. This is achieved by the provision of a graded radiation absorber in conjunction with a scintillation camera which makes it possible to use Compton interactions in a scintillation crystal to form the image by absorbing scattered radiation in the object under study which would otherwise be indistinguishable from Compton interactions in the crystal. Such graded absorbers have been useful in other applications as described by P. R. Bell, "The Scintillation Method", Beta and Gamma Spectroscopy, Chapter V, p. 141, edited by Kai Siegbahn and published by Interscience Publishers Inc., 1955.

As previously suggested, gamma rays emitted by a positron annihilation may travel in opposite directions and be detected by the dual scintillation crystals of a positron imaging system to contribute to the photopeak of primary radiation. As also suggested, one or both of the gamma rays may pass through the crystal with no interaction at all, in which case there is no recordation of the positron events. On the other hand, one or both of the gamma rays may interact with the crystal to yield only a portion of the energy to the crystal in the generation of a flash of light. Such an interaction is termed a Compton event and necessarily produces a flash of light of lower intensity directly proportional to the energy lost in the crystal by virtue of the Compton interaction. The gamma rays from the positron annihilation may undergo yet another alternative interaction in that one or both of the gamma rays may interact with surrounding material in the object in which they originate, thereby losing part of their energy. If thereafter such a gamma ray interacts with a scintillation crystal of the positron imaging system, it is indistinguishable from a Compton event, although unlike a Compton event, its point of interaction in the crystal bears no significant relation to its point of origin in the object under investigation. In the past, only the photopeak interactions have been used in positron cameras since scattered radiation within the object under study produces scintillations indistinguishable from those produced by Compton events. However, Compton events are potentially useful for image formation, since in each case, the centroid of the light emitted during the scintillation corresponds quite closely to the location at which the gamma ray enters the crystal. To the contrary, scattered radiation is not potentially useful, since a gamma ray of a positron event may travel some distance before interaction in surrounding material.

Accordingly, pursuant to the present invention, scattered radiation is masked from the scintillation detectors, thereby allowing a plurality of separate acceptable ranges of radioactive energy to be defined, in turn allowing the utilization of Compton events for use in image formation.

BRIEF DESCRIPTION OF THE INVENTION

The present invention may be described with greater clarity by reference to the accompanying drawings in which FIG. 1 is a block diagram of a positron imaging system modified according to this invention.

DETAILED DESCRIPTION OF THE INVENTION

Figure 1:
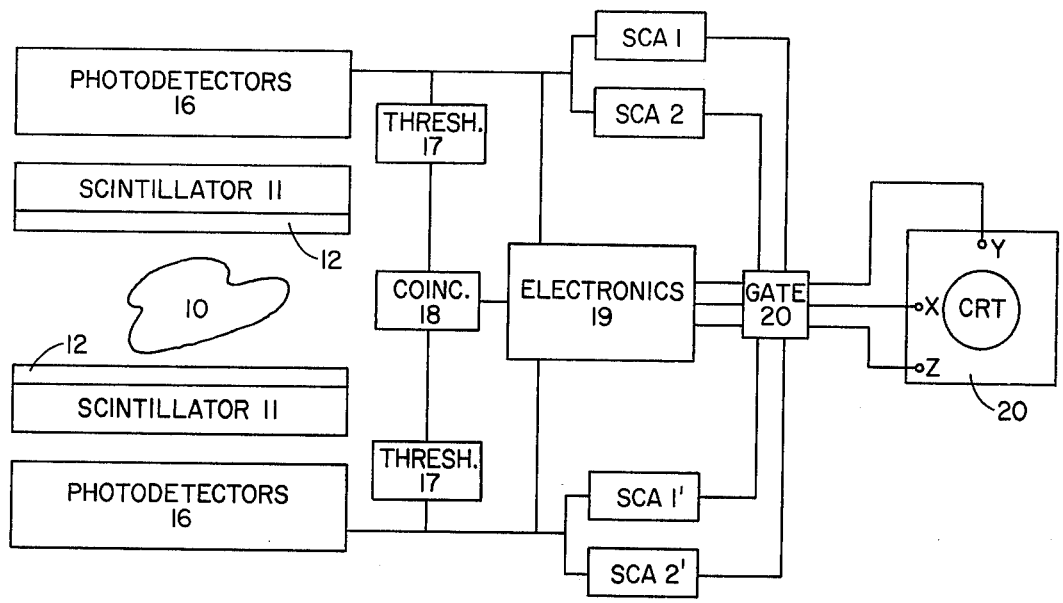
Figure 2:
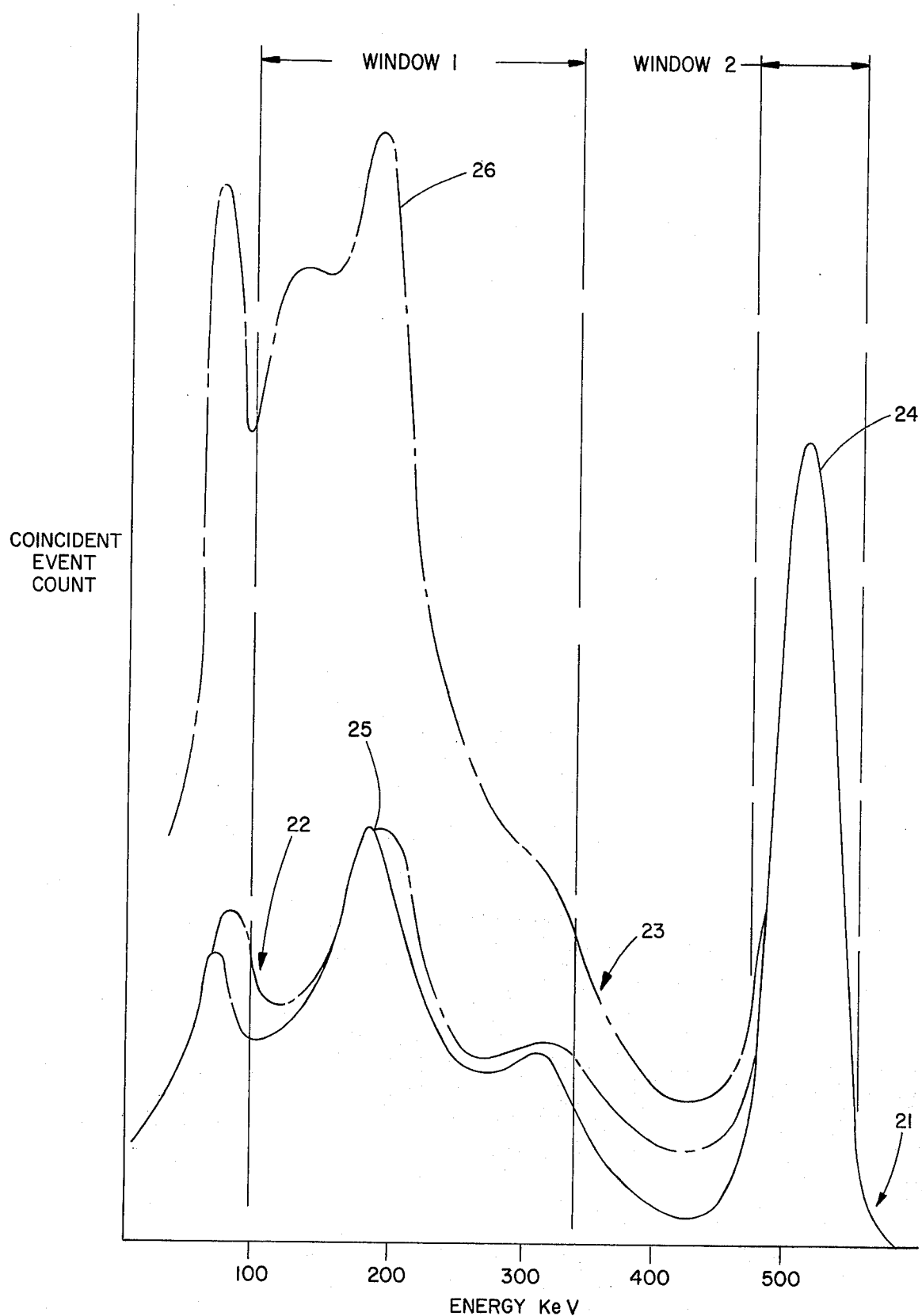
FIG. 2 illustrates the energy discrimination achieved utilizing the device of FIG. 1.

Referring now to FIG. 1, there is illustrated a positron imaging scintillation camera system. This system may be of the type described by Alexander Gottschalk and Hal O. Anger in "Progress in Radioisotope Scanning: Clinical Application of the Scintillation Camera", *Progress in Atomic Medicine*, Grune and Stratton, Inc., 1965, at pages 79–82, but modified and improved as specifically noted herein. The positron imaging camera of FIG. 1 employs two scintillation detectors, each including a disc 11 formed of thallium activated sodium iodide 11½ inches in diameter and one-half inch in thickness. Each scintillation detector also includes an array of photodetectors 16. The photodetectors in each array are arranged to view overlapping areas of the associated scintillator 11. The scintillation camera system of FIG. 1 is used to register on a cathode ray tube 20 the distribution of positron annihilations from an object under study, typically an organ of interest of a living subject which has injested an identified positron emitter. Each of the photodetector arrays 16 is connected to a threshold circuit 17. If the combined magnitude of electrical pulses from each photodetector array 16 exceeds a threshold magnitude established by the threshold circuit 17, an input is provided to the coincidence detection circuit 18. Upon detecting coincident emissions from the dual scintillation detectors, the coincidence detection circuit 18 gates an electronic pulse processing unit 19. When gated, electronic processing unit 19 receives inputs from each of the photodetector arrays 16. From these inputs, pulse processing unit 19 computes the position in rectilinear coordinates of the radioactive event creating the coincident outputs from photodetector arrays 16. The pulse processing unit 19 produces an output which, upon gate actuation, is passed to the beam deflection and actuation circuits of a cathode ray tube 20. By deflection of the cathode ray beam, the position of a positron annihilation is registered in the cathode ray tube 20. Integration of the registered positions of the accepted events, by means of photographic film exposed to the face of the cathode ray tube 20, produces a registration of the distribution of positron annihilations occurring in the object 10. In contrast with other conventional positron imaging scintillation camera systems, the present invention employs a plurality of single channel analyzers in association with each photodetector array 16. These single channel analyzers are depicted as SCA's 1 and 2 in association with one photodetector array 16 and as SCA's 1' and 2' in association with the other photodetector array 16. The SCA's define a plurality of discrete channels of acceptable ranges of radiation energy, identified respectively as window 1 and window 2 in FIG. 2. While only two separate channels are defined in the embodiment illustrated, it is to be understood that any plural number of channels may be employed to advantage, depending upon the positron emitter utilized, background radiation, and other factors. It is necessary only that a plural number of channels are defined, and that these channels are separate and distinct from each other as illustrated in FIG. 2. The upper and lower discriminator settings of window 1 and window 2 (defined by the settings of SCA 1 and 1' and SCA 2 and 2' respectively) are the same for both of the scintillation detectors, so that the discriminator settings for SCA 1 are identical to those of SCA 1' and the discriminator settings of SCA 2 are identical to those of SCA 2'.

Incident to the provision of the dual single channel analyzers in association with each scintillation detector, there is provided a gating circuit 20 which, when enabled, allows CRT 20 to function. The gating circuit 20 is enabled by a coincident input from each of the scintillation detectors through either of the single channel analyzers associated therewith. That is, circuit 20 will be gated by inputs from any of the following combinations of devices: SCA 1 and SCA 1', SCA 1 and SCA 2', SCA 2 and SCA 1', and SCA 2 and SCA 2'.

Figure 3:
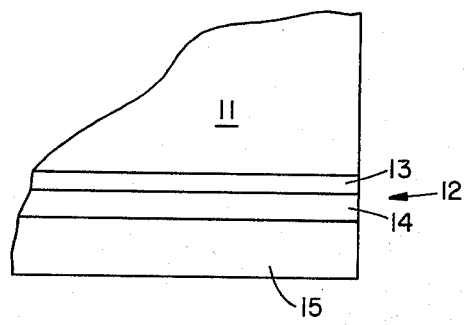
FIG. 3 is an enlarged view of a portion of the apparatus of FIG. 1.

Another aspect in which the device of FIG. 1 differs from a conventional positron scintillation imaging device is in the provision of the graded radiation absorber 12. The graded radiation absorber 12 is comprised of a layer 15 of a first metal for preferentially absorbing radiation in an inverse relationship with the energy level thereof. The layer 15 is positioned proximate to the object 10, from which gamma radiation emanates, and remote from the scintillation crystal 11. A layer 14 of a second metal is also provided for preferentially absorbing radiation of an energy corresponding to that of a secondary radiation emitted by the layer 15. The layer 14 is positioned less proximate to the object 10 and less remote from the scintillation crystal 11. It may also be advantageous to provide a layer 13 of a third metal for preferentially absorbing radiation of an energy corresponding to that of secondary radiation emitted by the layer 14. In this case, the layer 13 is positioned proximate to the scintillation crystal 11 and remote from the object 10. In the configuration depicted in FIG. 3, a suitable construction was achieved when the layer 15 was formed of lead and was 1.27 millimeters in thickness, the layer 14 was formed of tin and was 0.76 millimeters thick, and the layer 13 was formed of copper 0.25 millimeters thick.

In choosing materials from which to construct the graded absorber, it should be kept in mind that the effectiveness of absorption is a function of the atomic number and of the density of the metal used. In general, the higher the density and the larger the atomic number, the larger will be the attenuation coefficient. Thus, for example, lead has a higher attenuation coefficient than copper. Although lead and tungsten have similar attenuation coefficients (the one for lead being slightly greater) for equal thicknesses, tungsten will stop more gamma rays than lead as a result of its higher density.

The purpose of the graded radiation shielding is to prevent scattered radiation in the object 10 from reaching the scintillation crystal 11 while not stopping the primary radiation from the positron annihilations from reaching the scintillation crystals 11. There are two basic considerations in shielding construction. First, the attenuation of the primary gamma rays must be relatively small compared to the attenuation of the lower energy gamma rays. Secondly, secondary x-ray radiation emitted by the shielding must be minimized. By virtue of the first consideration, a large number of the gamma rays due to scattering within the object 10 will be absorbed, since the energy of these scattered gamma rays will be lower than the energy of the primary gamma rays of interest. Most materials will tend to absorb gamma rays of lower energy more strongly than those of higher energy. That is, the degree of gamma radiation absorption will bear an inverse relationship to the energy level of impinging gamma rays. However, in absorbing the lower energy gamma rays, provision must be made for the elimination of various characteristic radiation emitted by the absorber. This characteristic radiation is typically secondary x-ray radiation and is called K x-rays. The energy of a K x-ray is dependent upon the atomic number Z of the interacting material. The higher the atomic number the higher the K x-ray energy. There is a sharp decrease in the absorption power of the material for incident gamma ray energies below the K-edge. Physically the K-edge results from the removal of an atomic electron from the innermost electron shell in an atom of the shielding material as a result of the energy given up by an absorbed gamma ray. This implies that a shield composed of a single element should not be used, but rather a stack or series of layers of different elements will provide a more effective shielding means. In general, the layer that is most distant from the detector surface should have the highest atomic number. Since the K-edge of this material will correspond to the highest input gamma ray energy, it will be most effective in scattered gamma radiation of higher energy levels. Proceeding toward the scintillator 11, the layers will have a smaller atomic number. The characteristic x-rays of these layers will therefore be of increasingly lower energies. The layer 13 adjacent to the scintillator 11 should have a characteristic x-ray energy of a level less than that established as the threshold by the threshold circuits 17.

Curve 21 in FIG. 2 illustrates a typical spectrum from a point source of a positron emitter. The curve 21 includes a primary radiation peak 24 as well as a large area 25 comprised mainly of Compton scattering. If the point source of radiation is surrounded by a scattering material, such as the bodily organ 10 in FIG. 1, a radiation spectrum 23 is produced which differs markedly from the spectrum 21. This difference is primarily due to the scattered radiation in the area indicated at 26. The total number of events detected in the spectrum 23 is increased over the number detected in a crystal 11 from a point source of radiation. These additional events are detected as scattered radiation at 26 when the point source is surrounded by scattering material. The resulting distortion of the spectrum 21 has heretofore limited the use of positron imaging to only that radiation falling within window 2 in FIG. 2. However, by employing the graded radiation absorber of the present invention, a spectrum 22 of coincident events is produced even when a point source of radiation is surrounded by scattering material such as the organ 10. As is apparent from FIG. 2, the spectrum 22 closely approximates the spectrum 21. Moreover, a second window, designated as window 1 in FIG. 2, can be utilized to increase dramatically the number of positron events which contribute useful information for image formation.

By using Compton coincidences in the manner depicted, the useful count rate in positron imaging may be increased by at least a factor of 3, even using conservative estimates, without any increase in the administered radiation dose.

While only a single embodiment of the invention has been described, it will be appreciated that various alternative embodiments may be substituted without departing from the scope of the invention as defined in the claims.

We claim:

1. In a positron imaging scintillation camera for detecting the radioactive distribution of positron events within an organ of interest of a living subject utilizing dual scintillation detectors positioned on opposite sides of said organ of interest and registration means for recording positron events, the improvement comprising continuous, uniform graded absorption shielding means positioned between each of said detectors and the aforesaid organ of interest, discrimination means defining at least two separate acceptable ranges of radioactive energy, and coincidence gating means connected to said dual detectors for permitting the registration of only those radioactive events which are detected in coincidence by said dual detectors.

2. In a positron imaging scintillation camera for detecting the radioactive distribution of positron events within an organ of interest of a living subject utilizing dual scintillation detectors positioned on opposite sides of said organ of interest and registration means for recording positron events, the improvement comprising continuous, uniform graded absorption shielding means comprised of a layer of a first metal for preferentially absorbing radiation in an inverse relationship with the energy level thereof positioned remote from a one of said scintillation detectors, and a layer of a second metal for preferentially absorbing radiation of an energy corresponding to that of a secondary radiation emitted by said first layer and positioned less remote from said one of said scintillation detectors positioned between each of said detectors and the aforesaid organ of interest, discrimination means defining at least two separate acceptable ranges of radioactive energy, and coincidence gating means connected to said dual detectors for permitting the registration of only those radioactive events which are detected in coincidence by said dual detectors.

3. In a scintillation camera, the improvement comprising a graded radiation absorber for use in selectively absorbing gamma radiation comprising a layer of a first metal for preferentially absorbing radiation in an inverse relationship with the energy level thereof positioned proximate to a source of gamma radiation, and a layer of a second metal for preferentially absorbing radiation of an energy corresponding to that of secondary radiation emitted by said first layer and positioned less proximate to said source of gamma radiation.

4. The scintillation camera of claim 3 wherein said graded radiation absorber further comprises a layer of a third metal for preferentially absorbing radiation of an energy corresponding to that of secondary radiation emitted by said layer of said second metal and positioned remote from said soure of gamma radiation.

5. The scintillation camera of claim 4 wherein said first metal is lead, said second metal is tin, and said third metal is copper.

6. In a scintillation camera for use in detecting positron emissions from a subject positioned between two scintillation detectors and for registering the distribution of positron annihilations therein, the improvement comprising continuous, uniform radiation absorption means disposed between said scintillation detectors and said subject for selectively attenuating low energy radiation, discrimination means defining a plurality of discrete channels of acceptable ranges of radiation energy, and coincidence detection means for enabling registration of positron annihilations only upon detecting coincident radioactive events lying in an acceptable energy range from said scintillation detectors.

7. In a positron imaging device employing radiation detection means for registering the distribution of positron annihilations within an object, the improvement comprising a continuous, uniform graded radiation absorption means disposed between said object and said radiation detection means, and discrimination means defining a plurality of discrete radiation energy channels within which radiation emitted in response to positron annihilations must lie to be acceptable for registration.

* * * * *